(12) United States Patent
Matsuzawa et al.

(10) Patent No.: US 9,428,715 B2
(45) Date of Patent: Aug. 30, 2016

(54) COMPOSITION FOR CLEANSING AGENT AND CLEANSING AGENT

(71) Applicant: The Nisshin OilliO Group, Ltd., Tokyo (JP)

(72) Inventors: Makoto Matsuzawa, Yokohama (JP); Azusa Takanashi, Yokohama (JP); Minaho Komori, Yokohama (JP); Aki Gotou, Yokohama (JP)

(73) Assignee: The Nisshin OilliO Group, Ltd., Tokyo (JP)

( * ) Notice: Subject to any disclaimer, the term of this patent is extended or adjusted under 35 U.S.C. 154(b) by 0 days.

(21) Appl. No.: 14/343,944

(22) PCT Filed: Nov. 7, 2012

(86) PCT No.: PCT/JP2012/078856
§ 371 (c)(1),
(2) Date: Mar. 10, 2014

(87) PCT Pub. No.: WO2013/069690
PCT Pub. Date: May 16, 2013

(65) Prior Publication Data
US 2014/0323386 A1 Oct. 30, 2014

(30) Foreign Application Priority Data

Nov. 7, 2011 (JP) ................................. 2011-243373

(51) Int. Cl.
| | |
|---|---|
| *C11D 3/20* | (2006.01) |
| *A61Q 19/10* | (2006.01) |
| *C11D 3/37* | (2006.01) |
| *A61K 8/81* | (2006.01) |
| *A61Q 5/02* | (2006.01) |
| *A61K 8/85* | (2006.01) |

(52) U.S. Cl.
CPC ............ *C11D 3/2086* (2013.01); *A61K 8/8135* (2013.01); *A61K 8/85* (2013.01); *A61Q 5/02* (2013.01); *A61Q 19/10* (2013.01); *C11D 3/2093* (2013.01); *C11D 3/3715* (2013.01)

(58) Field of Classification Search
None
See application file for complete search history.

(56) References Cited

U.S. PATENT DOCUMENTS

| | | | |
|---|---|---|---|
| 2005/0089542 A1 | 4/2005 | Ferrari | |
| 2009/0197786 A1* | 8/2009 | Perry et al. | 510/191 |

FOREIGN PATENT DOCUMENTS

| | | |
|---|---|---|
| JP | 05-170622 A | 7/1993 |
| JP | 06-097142 A | 4/1994 |
| JP | 2000-204032 A | 7/2000 |
| JP | 2001-526197 A | 12/2001 |
| JP | 2002-531684 A | 9/2002 |
| JP | 2003275573 A | 9/2003 |
| JP | 2004-210704 A | 7/2004 |
| JP | 2004-277400 A | 10/2004 |
| JP | 2005-516045 A | 6/2005 |
| JP | 2006-199697 A | 8/2006 |
| JP | 2006-335673 A | 12/2006 |
| JP | 2007145770 A | 6/2007 |
| JP | 2007254334 A | 10/2007 |
| JP | 2008-231346 A | 10/2008 |
| JP | 2009013144 A | 1/2009 |
| JP | 2011-506556 A | 3/2011 |
| WO | 9702002 A2 | 1/1997 |
| WO | 2006/080389 A1 | 8/2006 |
| WO | 2011/111854 A1 | 9/2011 |
| WO | 2011/118497 A1 | 9/2011 |
| WO | 2012/063727 A1 | 5/2012 |

OTHER PUBLICATIONS

Japanese Patent Office, International Search Report issued in Application No. PCT/JP2012/078856, mailed Dec. 4, 2012, 4 pp.
European Search Report issued in European Patent Application No. 12847946.6, mailed Jun. 19, 2015, 9 pages.
Japanese Patent Office; Office Action in Japanese Patent Application No. 2013-543006 dated Jun. 14, 2016; 10 pages.
Japanese Patent Office; Office Action in Japanese Patent Application No. 2013-543006 dated Jun. 10, 2016; 10 pages.

* cited by examiner

*Primary Examiner* — Necholus Ogden, Jr.
(74) *Attorney, Agent, or Firm* — Wood, Herron & Evans, LLP

(57) ABSTRACT

The present invention relates to a composition for a cleansing agent comprising a component (A) in the form of an ionic surfactant and a component (B) in the form of one or more types of compounds selected from the group consisting of a hydroxystearic acid polymer and an esterification reaction product of a hydroxystearic acid polymer. According to the present invention, a composition for a cleansing agent can be provided that has favorable foaming power and foam quality, is easily rinsed during cleansing, is free of stickiness after cleansing and allows the obtaining of a moist feeling.

6 Claims, No Drawings

COMPOSITION FOR CLEANSING AGENT AND CLEANSING AGENT

TECHNICAL FIELD

The present invention relates to a composition for a cleansing agent that has favorable foaming power and foam quality, is easily rinsed during cleansing, is free of stickiness after cleansing and allows the obtaining of a moist feeling.

The present application claims priority on the basis of Japanese Patent Application No. 2011-243373 filed in Japan on Nov. 7, 2011, the contents of which are incorporated herein by reference.

BACKGROUND ART

Skin and hair cleansing agents have recently been required to not only demonstrate cleansing strength, but also demonstrate foam qualities such as superior foaming power, foam fineness, elasticity and staying power, as well as a superior feeling after cleansing. Although fatty acid soaps and amino acid-based surfactants are frequently used for the main ingredients of skin and hair cleansing agents, in the case of using these surfactants, although foaming power was superior, foam quality and a moist feeling after rinsing were inadequate.

Examples of cleansing agents having superior cleansing strength as well as a favorable feeling after cleansing include a cleansing agent having an improved feel during use in the form of the cleansing agent containing an anionic surfactant, an amphoteric surfactant and 12-hydroxystearic acid disclosed in Patent Document 1. In addition, an aqueous skin cleansing agent is disclosed in Patent Document 2 that contains a foamable surfactant, a hydrocarbon-based paste-like oily agent, and a non-hydrocarbon-based paste-like oily agent. Patent Document 3 discloses a cleansing agent containing a hydroxyalkyl ether carboxylate and an oily component having a hydration rate of 100%. Moreover, Patent Document 4 discloses a skin cleanser composition containing a higher fatty acid salt, an amino acid-based polymer, and two or more types of water-soluble polymers having different ionicities.

On the other hand, hydroxystearic acid polymers have superior pigment dispersibility and are used in cosmetics. For example, Patent Document 5 discloses a liquid cosmetic characterized by containing (a) an extender powder, (b) 0.1% by weight to 30% by weight of an oily agent, and (c) 0.001% by weight to 3% by weight of polyhydroxystearic acid, and a hydroxystearic acid polymer is incorporated for the purpose of improving wettability of the powder and oily agent.

In addition, Patent Document 6 discloses an esterification reaction product obtained by esterifying dipentaerythritol and 12-hydroxystearic acid polymer, wherein the hydroxyl value of the aforementioned esterification reaction product is 20 mg KOH/g to 70 mg KOH/g, and the acid value is 3 mg KOH/g or less. Since the aforementioned esterification reaction product demonstrates high water holding properties and has favorable pigment dispersibility, use of the aforementioned esterification reaction product allows the obtaining of oil-in-water-type emulsion cosmetics and water-in-oil-type emulsion cosmetics that incorporate a large amount of water (and/or polyvalent alcohol) and demonstrate superior water retention stability and temporal stability.

PRIOR ART DOCUMENTS

Patent Documents

[Patent Document 1] Japanese Unexamined Patent Application, First Publication No. H5-170622

[Patent Document 2] Japanese Unexamined Patent Application, First Publication No. 2006-335673

[Patent Document 3] Japanese Unexamined Patent Application, First Publication No. 2008-231346

[Patent Document 4] Japanese Unexamined Patent Application, First Publication No. 2004-210704

[Patent Document 5] Japanese Unexamined Patent Application, First Publication No. 2004-277400

[Patent Document 6] International Publication No. WO 2006/080389

DISCLOSURE OF THE INVENTION

Problems to be Solved by the Invention

Although the cleansing agents described in Patent Documents 1 to 4 demonstrate cleansing strength and feel during use that are superior to that of the prior art, their foaming power, foam quality and moist feeling after cleansing were inadequate.

In addition, there is no description or suggestion in Patent Documents 5 and 6 that favorable foaming power and foam quality, ease of rinsing during cleansing, absence of stickiness after cleansing and a moist feeling are obtained by incorporating a hydroxystearic acid polymer or esterification reaction product of a hydroxystearic acid polymer in a cleansing agent.

With the foregoing in view, there was a desire to develop a cleansing agent that has favorable foaming power and foam quality, is easily rinsed during cleansing, is free of stickiness after cleansing and allows the obtaining of a moist feeling.

An object of the present invention is to provide a composition for a cleansing agent that has favorable foaming power and foam quality, is easily rinsed during cleansing, is free of stickiness after cleansing and allows the obtaining of a moist feeling.

Means for Solving the Problems

As a result of conducting extensive studies to solve the aforementioned problems, the inventors of the present invention found that a cleansing agent that has favorable foaming power and foam quality, is easily rinsed during cleansing, is free of stickiness after cleansing and allows the obtaining of a moist feeling can be obtained by incorporating a polymer of hydroxystearic acid or an esterification reaction product thereof in a cleansing agent, thereby leading to completion of the present invention.

Namely, the present invention provides the following:

(1) a composition for a cleansing agent, including: a component (A) in the form of an ionic surfactant, and a component (B) in the form of one or more types of compounds selected from the group consisting of a hydroxystearic acid polymer and an esterification reaction product of a hydroxystearic acid polymer;

(2) the composition for a cleansing agent described in (1), wherein the component (B) is the hydroxystearic acid polymer;

(3) the composition for a cleansing agent described in (1) or (2), wherein the average number of monomers of the hydroxystearic acid polymer is 2 to 12;

(4) the composition for a cleansing agent described in (1), wherein dipentaerythrityl tripolyhydroxystearate is contained as component (B);

(5) a cleansing agent containing the composition for a cleansing agent described in any of (1) to (4); and (6) a cleansing agent, including: a component (A) in the form of an ionic surfactant, and a component (B) in the form of one or more types of compounds selected from the group consisting of a hydroxystearic acid polymer and an esterification reaction product of a hydroxystearic acid polymer.

Effects of the Invention

According to the present invention, a composition for a cleansing agent that has favorable foaming power and foam quality, is easily rinsed during cleansing, is free of stickiness after cleansing and allows the obtaining of a moist feeling, and a cleansing agent containing the same, can be provided.

BEST MODE FOR CARRYING OUT THE INVENTION (Composition for a Cleansing Agent)
The composition for a cleansing agent of the present invention is characterized by comprising the following components (A) and (B):
component (A): ionic surfactant, and
component (B): at least one compound selected from the group consisting of a hydroxystearic acid polymer and an esterification reaction product of a hydroxystearic acid polymer.

There are no particular limitations on the ionic surfactant of component (A) provided it is an ionic surfactant capable of being incorporated in various types of cosmetics including cleansing agents, and one type or two or more types of anionic surfactants, cationic surfactants or amphoteric surfactants can be used.

Examples of anionic surfactants include fatty acid soaps such as soap base, sodium laurate or sodium palmitate, alkyl sulfate ester salts having 8 to 22 carbon atoms such as sodium lauryl sulfate or potassium lauryl sulfate, alkyl ether sulfate ester salts such as polyoxyethylene (POE)-triethanolamine lauryl sulfate or POE-sodium lauryl sulfate, N-acyl sarcosinates such as sodium lauroyl sarcosinate, fatty acid amide sulfonates having 8 to 22 carbon atoms such as sodium N-myristyl-N-methyl taurate, sodium methyl coconut oil fatty acid taurate (also referred to as sodium methyl cocoyl taurate) or sodium methyl lauryl taurate, phosphate ester salts such as POE-sodium oleyl ether phosphate or POE-stearyl ether phosphate, sulfosuccinates such as sodium di(2-ethyl-hexyl)sulfosuccinate, sodium monolauroyl monoethanolamide polyoxyethylene sulfosuccinate or sodium lauryl polypropylene glycol sulfosuccinate, alkyl benzene sulfonates such as sodium linear dodecyl benzene sulfonate, triethanolamine linear dodecyl benzene sulfonate or linear dodecyl benzene sulfonate, N-acyl glutamates such as monosodium N-lauroyl glutamate, disodium N-stearoyl glutamate or monosodium N-myristyl-L-glutamate, N-acyl glycinates such as potassium N-cocoyl glycinate or sodium N-stearoyl glycinate, fatty acid ester sulfate ester salts having 8 to 22 carbon atoms such as sodium hydrogenated coconut oil fatty acid glyceryl sulfate, sulfonated oils such as turkey red oil, POE-alkyl ether carboxylates, POE-alkyl allyl ether carboxylates, α-olefin sulfonates, fatty acid ester sulfonates having 8 to 22 carbon atoms, secondary alcohol sulfate ester salts, fatty acid alkyloyl amide sulfate ester salts having 8 to 22 carbon atoms, sodium lauroyl ethanolamide succinate, ditriethanolamine N-palmitoyl aspartate and sodium casein.

In the composition for a cleansing agent of the present invention, fatty acid soaps, fatty acid amide sulfonates having 8 to 22 carbon atoms, alkyl sulfate ester salts, N-acyl glutamates and N-acyl glycinates are used preferably, and fatty acid soaps, N-acyl glutamates, fatty acid amide sulfonates having 8 to 22 carbon atoms and N-acyl glycinates are used more preferably. Among these, fatty acid amide sulfonates having 8 to 22 carbon atoms are particularly preferable, and sodium methyl coconut oil fatty acid taurate (sodium methyl cocoyl taurate) is most preferable.

The aforementioned anionic surfactants may be used alone or two or more types may be used in combination.

Examples of cationic surfactants include alkyl trimethyl ammonium salts such as stearyl trimethyl ammonium chloride or lauryl trimethyl ammonium chloride, dialkyl dimethyl ammonium salts such as distearyl dimethyl ammonium chloride, alkyl pyridinium salts such as poly(N,N'-dimethyl-3,5-methylene piperidinium)chloride or cetylpyridinium chloride, alkyl quaternary ammonium salts, alkyl dimethyl benzyl ammonium salts, alkyl isoquinolinium salts, dialkyl morpholinium salts, POE-alkyl amines, alkyl amine salts, polyamine fatty acid derivatives, amyl alcohol fatty acid derivatives, benzalkonium salts and benzethonium chloride.

These cationic surfactants may be used alone or two or more types may be used in combination.

Examples of amphoteric surfactants include imidazoline-based amphoteric surfactants such as sodium 2-undecyl-N,N,N-(hydroxyethylcarboxymethyl)-2-cocoyl-2-imidazoline or 2-cocoyl-2-imidazolinium hydroxide-1-carboxyethyloxy-2-sodium, and betaine-based surfactants such as 2-heptadecyl-N-carboxymethyl-N-hydroxyethyl imidazolium betaine, lauryl dimethylaminoacetate betaine, alkyl betaines, amidobetaines, alkylamidobetaines or sulfobetaines. In the composition for a cleansing agent of the present invention, betaine-based surfactants and imidazoline-based surfactants are used preferably, betaine-based surfactants are used more preferably, and cocamidopropyl betaine is used particularly preferably.

These amphoteric surfactants may be used alone or two or more types may be used in combination.

In the composition for a cleansing agent of the present invention, the content of the ionic surfactant of component (A) is a concentration that is sufficient for demonstrating cleansing effects, and can be suitably determined in consideration of such factors as the type of cleansing agent in which the aforementioned composition for a cleansing agent is incorporated and the types and amounts of other incorporated components. For example, the composition for a cleansing agent of the present invention can contain 5% by weight to 60% by weight, preferably 5% by weight to 50% by weight, and more preferably 5% by weight to 40% by weight of the ionic surfactant of component (A), relative to the total weight of the cleaning agent composition of the present invention. In the case the incorporated amount of ionic surfactant is less than 5% by weight, relative to the total weight of the composition for a cleansing agent, it becomes difficult to obtain functions such as washability or foamability, while in the case the incorporated amount exceeds 60% by weight, there is the risk of gelling of the resulting composition, thereby making it difficult to obtain a stable formulation. Namely, as a result of incorporating component (A) at 5% by weight to 60% by weight, relative to the total weight of the composition for a cleansing agent, functions such as washability and foamability of the composition for a cleansing agent are easily obtained, the resulting composition does not undergo gelling, and a stable formulation is easily obtained, thereby making this preferable.

An amphoteric surfactant or anionic surfactant is preferably used for the ionic surfactant of component (A). Moreover, a fatty acid soap, fatty acid amide sulfonate having 8 to 22 carbon atoms, alkyl sulfate ester salt, N-acyl glutamate, N-acyl glycinate, betaine-based surfactant or imidazoline-based surfactant is used more preferably, and a fatty acid soap, N-acyl glutamate, N-acyl glycinate, betaine-based surfactant or imidazoline-based surfactant is used particularly preferably.

In addition, in the composition for a cleansing agent of the present invention, component (A) not only includes that added in the composition for a cleansing agent in the form of an ionic surfactant, but also includes a neutral salt formed during the course of production of the composition for a cleansing agent.

The composition for a cleansing agent of the present invention may also contain as component (B) one or more types of compounds selected from the group consisting of hydroxystearic acid polymers and esterification reaction products of hydroxystearic acid polymers. One type or two or more types of hydroxystearic acid polymers may only be contained as component (B), one type or two or more types of esterification reaction products of hydroxystearic acid polymers may only be contained, or one type or two or more types of hydroxystearic acid polymers and one type or two or more types of esterification reaction products of hydroxystearic acid polymers may be contained.

The hydroxystearic acid polymer refers to a polymer obtained by polymerizing a plurality of monomers in the form of hydroxystearic acid. Hydroxystearic acid has a single hydroxyl group in a molecule thereof, and the polymerization reaction of hydroxystearic acid is a reaction in which a hydroxyl group or carboxyl group in a molecule of hydroxystearic acid is esterified with a carboxyl group or hydroxyl group in a molecule of another hydroxystearic acid, or in other words, an interesterification reaction.

Examples of hydroxystearic acid polymers include polymers of 12-hydroxystearic acid.

Polymers of 12-hydroxystearic acid can be produced by, for example, the polymerization reaction indicated below.

12-hydroxystearic acid is charged into a reaction vessel followed by carrying out an esterification reaction (polymerization reaction) while stirring for 5 hours to 30 hours at a temperature of 180° C. to 220° C. in the presence or absence of acid, base or other metal catalyst and preferably in an organic solvent and/or gas that is inert in the reaction.

12-hydroxystearic acid obtained by hydrogenating ricinoleic acid, which is obtained by hydrolyzing castor oil, for example, can be used for the 12-hydroxystearic acid. In addition, a commercially available product can also be used for the 12-hydroxystearic acid, and examples of such products that can be used include 12-Hydroacid (trade name, Kokura Synthetic Industries, Ltd.), Hydroxystearic Acid (trade name, Kawaken Fine Chemicals Co., Ltd.), and Hydrogenated Castor Oil Fatty Acid (trade name, NOF CORPORATION).

The average degree of polymerization (the average number of monomers) of the 12-hydroxystearic acid polymer is preferably 2 to 12. Namely, in the present invention, the average number of monomers refers to the average degree of polymerization of a monomer in the form of 12-hydroxystearic acid. If the average degree of polymerization is within the aforementioned range, namely 2 to 12, foaming power, foam quality and feel during use improve. In addition, the average degree of polymerization of the 12-hydroxystearic polymer is more preferably 4 to 12 and most preferably 6 to 12. In order for the average degree of polymerization of the 12-hydroxystearic acid polymer to be within the aforementioned ranges, the average degree of polymerization can be adjusted by measuring the acid value of the reaction product during the polymerization reaction of 12-hydroxystearic acid. Namely, this can easily be carried out by sampling the reaction product during the polymerization reaction of 12-hydroxystearic acid, calculating the average degree of polymerization by measuring the acid value thereof, and discontinuing the esterification reaction (polymerization reaction) at the point the desired average degree of polymerization has been reached. Namely, by discontinuing the esterification reaction at the point the acid value of the reaction product of 12-hydroxystearic acid has reached 15.5 mg KOH/g to 105 mg KOH/g, a 12-hydroxystearic acid polymer can be obtained in which the average degree of polymerization thereof is 2 to 12.

Here, acid value refers to the number of mg of potassium hydroxide required to neutralize free fatty acid present in 1 g of the 12-hydroxystearic acid polymer.

An esterification reaction product of a hydroxystearic acid polymer is obtained by esterifying the aforementioned hydroxystearic acid polymer and alcohol. The alcohol used in the esterification reaction may be a monovalent alcohol or polyvalent alcohol. Examples of monovalent alcohols include methanol, ethanol, propanol, isopropanol, isobutyl alcohol and t-butyl alcohol. Examples of polyvalent alcohols include propylene glycol, glycerin, diglycerin, 1,3-butylene glycol, isoprene glycol, dipropylene glycol, polyethylene glycol, pentaerythritol, dipentaerythritol, neopentyl glycol and sorbitan. Among these, one type or two or more types of alcohols selected from glycerin, diglycerin, sorbitan, pentaerythritol and dipentaerythritol are preferable for the alcohol esterified with the hydroxystearic acid polymer, and dipentaerythritol is more preferable.

Namely, the esterification reaction product of a hydroxystearic acid polymer used as component (B) is preferably an esterification reaction product of dipentaerythritol and a hydroxystearic acid polymer, and more preferably dipentaerythrityl tripolyhydroxystearate.

In the present invention, the esterification reaction of an alcohol and 12-hydroxystearic acid polymer is specifically carried out in the following manner. An alcohol and the 12-hydroxystearic acid polymer are placed in a reaction vessel, and after carrying out an esterification reaction for 1 hour to 20 hours at a temperature of 200° C. to 220° C. in an inert organic solvent and/or gas, the product is purified to obtain an esterification reaction product of the alcohol and 12-hydroxystearic acid polymer.

A catalyst may be used as necessary in the aforementioned esterification reaction. Examples of catalysts include acid catalysts and alkoxides of alkaline earth metals, and in the case of using an acid catalyst or alkoxide of an alkaline earth metal, the amount used is preferably about 0.001% by weight to 1.0% by weight, relative to the total weight of the reaction raw materials.

Following the reaction, catalyst and unreacted raw materials can be removed by carrying out a known purification treatment such as water washing, deacidification with base, or adsorption treatment. Moreover, the resulting reaction product can be further purified by carrying out decolorization and deodorization treatment.

In this manner, an esterification reaction product can be obtained in the form of an odorless and colorless to pale yellow clear liquid. The resulting esterification reaction product can be used as a constituent of the cleansing agent to be subsequently explained.

For example, in the case of an esterification reaction between a hydroxystearic acid polymer and dipentaerythritol, the charged amount of 12-hydroxystearic acid polymer used in the aforementioned reaction is such that the value of the acid value thereof is within the range indicated below and is determined in consideration of reducing the amount of unreacted dipentaerythritol. Namely, the charged amount of 12-hydroxystearic acid polymer used in the esterification reaction is preferably 1 mole to 6 moles, more preferably 1.5 moles to 5 moles, and most preferably 2 moles to 4 moles, relative to 1 mole of dipentaerythritol.

As a result of adjusting the charging ratio in this manner, the appearance, viscosity and water holding property of the resulting esterification reaction product can be adjusted as necessary.

Here, water holding property refers to the property of being able to hold water, and can be evaluated based on hydration rate (%). In addition, viscosity refers to the value measured with a Brookfield viscometer or stress-controlled rheometer and the like.

The hydroxyl value of the esterification reaction product of the aforementioned hydroxystearic acid polymer used as component (B) and dipentaerythritol is preferably 20 mg KOH/g to 70 mg KOH/g, more preferably 20 mg KOH/g to 60 mg KOH/g, even more preferably 25 mg KOH/g to 50 mg KOH/g, and most preferably 30 mg KOH/g to 40 mg KOH/g. If the hydroxyl value is lower than 20 mg KOH/g, there are cases in which it is difficult to obtain a product having the target water holding property and dispersibility. In addition, if the hydroxyl value exceeds 70 mg KOH/g or is lower than 20 mg KOH/g, there are cases in which production may be difficult. Namely, if the hydroxyl value of the esterification reaction product of the hydroxystearic acid polymer and dipentaerythritol is 20 mg KOH/g to 70 mg KOH/g, an esterification reaction product having the target water holding property and dispersibility is easily produced, thereby making this preferable. The hydroxyl value of the esterification reaction product of the hydroxystearic acid polymer can be made to be within the aforementioned range by adjusting the usage ratio of the dipentaerythritol and 12-hydroxystearic acid polymer, or in other words, the charged amounts of the dipentaerythritol and 12-hydroxystearic acid polymer.

Here, hydroxyl value refers to the number of mg of potassium hydroxide required to acetylate hydroxyl groups contained in 1 g of an esterification reaction product of a hydroxystearic acid polymer.

The acid value of the esterification reaction product of the hydroxystearic acid polymer used as component (B) and the dipentaerythritol is preferably 3 mg KOH/g or less, or in other words 0 mg KOH/g to 3 mg KOH/g. An odor may be produced if the acid value exceeds 3 mg KOH/g. An example of a method for adjusting the acid value of the esterification reaction product of the hydroxystearic acid polymer to be within the aforementioned range consists of sampling the reaction product during the esterification reaction and measuring the acid value thereof, and discontinuing the esterification reaction at the point the acid value of the sample is 3 mg KOH/g or less.

The contents of the hydroxystearic acid polymer and esterification reaction product of the hydroxystearic acid polymer of component (B) in the composition for a cleansing agent of the present invention are concentrations that are sufficient for demonstrating effects that improve the foaming power, foam quality and feel during use of the cleansing agent in which the aforementioned composition for a cleansing agent is incorporated, and can be suitably determined in consideration of such factors as the type of cleansing agent in which the aforementioned composition for a cleansing agent is incorporated and the types and amounts of other incorporated components. For example, the composition for a cleansing agent of the present invention can contain 0.1% by weight to 15% by weight, preferably 0.5% by weight to 10% by weight, and more preferably 0.5% by weight to 8% by weight, of the hydroxystearic acid polymer and esterification reaction product of the hydroxystearic acid polymer of component (B) relative to the total weight of the composition for a cleansing agent. If the content of the hydroxystearic acid polymer and esterification reaction product of the hydroxystearic acid polymer of component (B) is 0.1% by weight to 15% by weight, relative to the total weight of the composition for a cleansing agent, foaming power and foam quality are favorable, there is no stickiness after cleansing and a moist feeling is obtained, thereby making this preferable.

The composition for a cleansing agent of the present invention can suitably incorporate as necessary various types of components typically used in composition for a cleansing agents provided they do not impair the effects of the present invention. Specific examples thereof include water-soluble polymers such as natural water-soluble polymers, semi-synthetic water-soluble polymers, synthetic water-soluble polymers and inorganic water-soluble polymers, ultraviolet absorbers, metal ion sequestering agents, dispersion media such as lower alcohols or polyvalent alcohols, monosaccharides, oligosaccharides and polysaccharides, organic amines, synthetic resin emulsions, preservatives, pH adjusters, vitamins, plant extracts, antioxidants, antioxidant assistants and fragrances. One type of these components can be used or two or more types can be used in combination.

Examples of natural water-soluble polymers include plant-based polymers such as gum arabic, tragacanth gum, galactan, gua gum, carob gum, carrageenan, pectin, quince seed (quince), algae colloid (brown algae extract), starch (rice, corn, potato or wheat starch), microorganism-based polymers such as dextran, succinoglucan or pullulan, and animal-based polymers such as collagen, casein, albumin or gelatin.

Examples of semi-synthetic water-soluble polymers include starch-based polymers such as carboxymethyl starch or methyl hydroxypropyl starch, cellulose-based polymers such as methyl cellulose, nitrocellulose, methyl hydroxypropyl cellulose, sodium cellulose sulfate, hydroxypropyl cellulose, carboxymethyl cellulose, carboxymethyl cellulose sodium, crystalline cellulose or cellulose powder, and alginic acid-based polymers such as sodium alginate and propylene glycol alginate.

Examples of synthetic water-soluble polymers include vinyl-based polymers such as polyvinyl alcohol, polyvinyl methyl ether, polyvinylpyrrolidone or carboxyvinyl polymer (Carbopol), copolymer-based polymers such as polyoxyethylene-polyoxypropylene copolymers, acrylic polymers such as sodium polyacrylate, polyethyl acrylate or polyacrylamide, polyethyleneimine and cationic polymers.

Examples of inorganic water-soluble polymers include bentonite, magnesium aluminum silicate (bee gum), laponite, hectorite and silicic anhydride.

Examples of ultraviolet absorbers include benzoic acid-based ultraviolet absorbers such as para-aminobenzoic acid (PABA), PABA monoglyceryl ester, N,N-dipropoxy-PABA ethyl ester, N,N-diethoxy-PABA ethyl ester, N,N-dimethyl-PABA ethyl ester or N,N-dimethyl-PABA butyl ester, anthranilic acid-based ultraviolet absorbers such as homomethyl-N-acetyl anthranilate, salicylic acid-based ultraviolet absorbers such as amyl salicylate, menthyl salicylate, homomethyl salicylate, octyl salicylate, phenyl salicylate, benzyl salicylate or p-isopropanol phenyl salicylate, cinnamic acid-based ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenyl cinnamate or glyceryl mono-2-ethylhexanoyl diparamethoxycinnamate, benzophenone-based ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octoxybenzophenone or 4-hydroxy-3-carboxybenzophenone, 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methylphenyl)benzotriazole, dibenzalazine, dianisoylmethane, 4-methoxy-4'-t-butyldibenzoylmethane, 5-(3,3-dimethyl-2-norbornylidene)-3-pentan-2-one, 2,4,6-trianilino-p-(carbo-2'-ethylhexyl-1'-oxy) 1,3,5-triazine and 4-tert-butyl-4'-methoxydibenzoylmethane. These ultraviolet absorbers may be used alone or two or more types may be used in combination.

Examples of metal ion sequestering agents include disodium edetate, edetates and hydroxyethane diphosphonate. These metal ion sequestering agents may be used alone or two or more types may be used in combination.

Examples of lower alcohols include methanol, ethanol, propanol, isopropanol, isobutyl alcohol and t-butyl alcohol.

Examples of polyvalent alcohols include propylene glycol, glycerin, diglycerin, 1,3-butylene glycol, isoprene glycol, dipropylene glycol, polyethylene glycol, pentaerythritol, dipentaerythritol, neopentyl glycol, sorbitol and sorbitan. Among these, glycerin, dipropylene glycol, sorbitol, propylene glycol, 1,3-butylene glycol and polyethylene glycol are used preferably, and glycerin, dipropylene glycol and sorbitol are used more preferably.

Examples of monosaccharides include trioses such as D-glyceraldehyde or dihydroxyacetone, tetroses such as D-erythrose, or D-treose, pentoses such as L-arabinose, D-xylose, L-lyxose, D-arabinose, D-ribose, D-ribulose, D-xylulose or L-xylulose, hexoses such as D-glucose, D-talose, D-psicose, D-galactose, D-fructose, L-galactose,L-mannose or D-tagatose, heptoses such as acyl heptose or heptulose, octoses such as octose, deoxy sugars such as 2-deoxy-D-ribose, 6-deoxy-L-galactose or 6-deoxy-L-mannose, amino sugars such as D-glucosamine, D-galactosamine, sialic acid, aminouronic acid or muraminic acid, and uronic acids such as D-glucuronic acid, D-mannuronic acid, L-gulonic acid, D-galacturonic acid or L-iduronic acid.

Examples of oligosaccharides include gentianose, umbeliferose, lactose, planteose, isolychnose, raffinose, lychnose, umbilicin, stachyose and verbascose.

Examples of polysaccharides include cellulose, chondroitin sulfate, dextrin, glucomannan, chitin, galactan, dermatan sulfate, glycogen, gum arabic, heparan sulfate, tragacanth gum, keratan sulfate, chondroitin, mucoitin sulfate, gua gum, dextran, keratosulfate, locust bean gum, succinoglucan and charoninic acid.

Examples of amino acids include neutral amino acids such as threonine or cysteine, and basic amino acids such as hydroxylysine. In addition, examples of amino acid derivatives include sodium acyl sarcosinate (sodium lauroyl sarcosinate), acyl glutamate, sodium acyl-β-alaninate and glutathione.

Examples of organic amines include monoethanolamine, diethanolamine, triethanolamine, morpholine, triisopropanolamine, 2-amino-2-methyl-1,3-propanediol and 2-amino-2-methyl-1-propanol.

Examples of synthetic resin emulsions include alkyl acrylate copolymer emulsions, alkyl methacrylate polymer emulsions, acrylic acid-alkyl acrylate copolymer emulsions, methacrylic acid-alkyl methacrylate copolymer emulsions, alkyl acrylate-styrene copolymer emulsions, alkyl methacrylate-styrene copolymer emulsions, vinyl acetate polymer emulsions, polyvinyl acetate emulsions, vinyl acetate-containing copolymer emulsions, vinylpyrrolidone-styrene copolymer emulsions and silicone-containing copolymer emulsions. These synthetic resin emulsions may be used alone or two or more types may be used in combination.

Examples of preservatives include methyl paraben, ethyl paraben, butyl paraben and phenoxyethanol. These preservatives may be used alone or two or more types may be used in combination.

Examples of pH adjusters include edetic acid, disodium edetate, sodium hydroxide, potassium hydroxide and triethanolamine. These pH adjusters may be used alone or two or more types may be used in combination.

Examples of vitamins include vitamin A, vitamin B1, vitamin B2, vitamin B6, vitamin E, vitamin K and derivatives thereof, pantothenic acid and derivatives thereof and biotin.

Examples of plant extracts include aloe vera, witch hazel, hamamelis, cucumber, lemon, lavender and rose extracts.

Examples of antioxidants include oil-soluble vitamin C derivatives, tocopherols and derivatives and salts thereof, dibutylhydroxytoluene, butylhydroxyanisole and gallic acid esters. These antioxidants may be used alone or two or more types may be used in combination.

Examples of antioxidant assistants include phosphoric acid, citric acid, maleic acid, malonic acid, succinic acid, fumaric acid, cephalin, hexametaphosphate, phytic acid and ethylenediamine tetraacetate.

An example of another aspect of the composition for a cleansing agent of the present invention is:

a composition for a cleansing agent containing:
component (A) in the form of an ionic surfactant,
component (B) in the form of one or more types of compounds selected from the group consisting of a hydroxystearic acid polymer and an esterification reaction product of a hydroxystearic acid polymer,
component (C) in the form of a dispersion medium, and water, wherein
the amount of the aforementioned component (A) is 5% by weight to 60% by weight,
the amount of the aforementioned component (B) is 0.1% by weight to 15% by weight,
the amount of the aforementioned component (C) is 1% by weight to 50% by weight, and
the amount of water is 5% by weight to 90% by weight, relative to the total weight of the composition for a cleansing agent, and
the total amount of each of the aforementioned components based on the total weight of the composition for a cleansing agent does not exceed 100% by weight.

An example of another aspect of the composition for a cleansing agent of the present invention is:

a composition for a cleansing agent containing:
component (A) in the form of one or more ionic surfactant selected from the group consisting of a fatty acid soap, fatty acid amide sulfonate, alkyl sulfate ester salt, N-acyl glutamate and N-acyl glycinate, component (B) in the form of one or more compounds selected from the group consisting of a hydroxystearic acid polymer and an esterification reaction product of a hydroxystearic acid polymer, component (C) in the form of one or more types of dispersion mediums selected from the group consisting of glycerin, dipropylene glycol, sorbitol, propylene glycol, 1,3-butylene glycol and polyethylene glycol, and water, wherein the amount of the aforementioned component (A) is 5% by weight to 50% by weight, the amount of the aforementioned component (B) is 0.5% by weight to 10% by weight, the amount of the aforementioned component (C) is 1% by weight to 40% by weight, and the amount of water is 5% by weight to 90% by weight, relative to the total weight of the composition for a cleansing agent, and the total amount of each of the aforementioned components based on the total weight of the composition for a cleansing agent does not exceed 100% by weight.

An example of another aspect of the composition for a cleansing agent of the present invention is:

a composition for a cleansing agent containing:

component (A) in the form of one or more types of anionic surfactant selected from the group consisting of a fatty acid soap, fatty acid amide sulfonate, alkyl sulfate ester salt, N-acyl glutamate and N-acyl glycinate, component (B) in the form of one or more compounds selected from the group consisting of a hydroxystearic acid polymer having the average number of monomers of 2 to 12 and dipentaerythrityl tripolyhydroxystearate, component (C) in the form of one or more types of dispersion mediums selected from the group consisting of glycerin, dipropylene glycol, sorbitol, propylene glycol, 1,3-butylene glycol and polyethylene glycol, and water, wherein the amount of the aforementioned component (A) is 5% by weight to 50% by weight, the amount of the aforementioned component (B) is 0.5% by weight to 10% by weight, the amount of the aforementioned component (C) is 1% by weight to 40% by weight, relative to the total weigh of the composition for a cleansing agent, and the amount of water is 5% by weight to 90% by weight, and the total amount of each of the aforementioned components relative to the total weight of the composition for a cleansing agent does not exceed 100% by weight.

(Cleansing Agent)

The cleansing agent in the present invention is composed of the previously described composition for a cleansing agent. The cleansing agent of the present invention can be used in facial cleansers, cleansing cosmetics, body shampoos, shampoos, hypoallergenic shampoos (baby shampoos), hypoallergenic body shampoos and pet cleansers. In addition, the cleansing agent of the present invention can also be preferably used in liquid laundry detergents, dishwashing liquids, liquid wall cleaners and various other types of cleansers.

There are no particular limitations on the form of the cleansing agent of the present invention, and it can be used in the form of, for example, a paste, gel, liquid, solid or mousse. Namely, the cleansing agent of the present invention can be used as a paste cleansing agent, gel cleansing agent, liquid cleansing agent, solid cleansing agent or mousse cleansing agent. Among these, it is preferably used in the form of a liquid, solid or mousse.

Since the cleansing agent of the present invention incorporates one or more types of compounds selected from the group consisting of a hydroxystearic acid polymer and an esterification reaction product of a hydroxystearic acid polymer, it has the characteristic of demonstrating favorable foaming power and foam quality in comparison with ordinary cleansing agents. Consequently, it is preferably used as a liquid, solid or mousse cleansing agent that is required to be used by lathering the cleansing agent while also requiring favorable foam quality.

In addition, the cleansing agent of the present invention can be produced by a conventionally known cleansing agent production method. In addition, a cleansing agent can also be realized by producing a cleansing agent containing one type or a plurality of types of any of the aforementioned component (A) and component (B) indicated as constituents of the composition for a cleansing agent of the present invention, followed by adding any remaining components or cleansing agent raw materials containing the same to the aforementioned cleansing agent.

EXAMPLES

Although the following provides a more detailed explanation of the present invention by indicating examples and comparative examples thereof, the present invention is not limited thereto.

Examples 1 to 6 and Comparative Examples 1 to 8

(Production Method)

Cleansing foams were obtained according to the formulations shown in Tables 1 to 3. More specifically, all of the components a in Tables 1 to 3 were mixed and dissolved at 70° C. to obtain mixture a. On the other hand, all of the components b in Tables 1 to 3 were mixed and dissolved at 70° C. to obtain mixture b. Mixture a was gradually added to mixture b at a temperature of 70° C. followed by carrying out a saponification reaction, and following completion of the saponification reaction, the reaction product was cooled while stirring to obtain a creamy cleansing foam.

The average number of monomers of the polyhydroxystearic acid (12-hydroxystearic acid) used in Tables 1 to 3 is 6. In addition, the dipentaerythrityl tripolyhydroxystearate used in Examples 1 and 4 is the esterification reaction product of polyhydroxystearic acid having an average number of monomers of 6 and dipentaerythritol.

In addition, the stearic acid, lauric acid and myristic acid of components were saponified with the potassium hydroxide of components b, and were present as ionic surfactants in the creamy cleansing foams.

(Evaluation)

Each of the creamy cleansing foams was evaluated for lathering ease, foam fineness, foam elasticity (viscosity), foam staying power, rinsing ease, residue after rinsing, greasiness after drying and moist feeling after drying. More specifically, 2 g of the creamy cleansing foams of the present invention were lathered with the palms of the hands, and after uniformly applying over the entire face, the face was washed for 10 seconds. Subsequently, the cleansing foam was rinsed off for 20 seconds with running water at 25° C. followed by drying with a towel. Evaluations were made by five expert panelists, and lathering ease, foam fineness, foam elasticity (viscosity), foam staying power, rinsing ease, residue after rinsing, greasiness after drying and moist feeling after drying were evaluated according to the evaluation criteria indicated below.

<Lathering Ease>
A: All 5 panelists indicated extremely favorable lathering.
B: 4 of 5 panelists indicated favorable lathering.
C: 3 of 5 panelists indicated favorable lathering.
D: 2 of 5 panelists indicated favorable lathering.
<Foam Fineness>
A: All 5 panelists indicated extremely fine foam.
B: 4 of 5 panelists indicated fine foam.
C: 3 of 5 panelists indicated fine foam.
D: 2 of 5 panelists indicated fine foam.
<Foam Elasticity>
A: All 5 panelists indicated extremely elastic foam.
B: 4 of 5 panelists indicated elastic foam.
C: 3 of 5 panelists indicated elastic foam.
D: 2 of 5 panelists indicated elastic foam.
<Foam Staying Power>
A: All 5 panelists indicated foam staying power.
B: 4 of 5 panelists indicated foam staying power.
C: 3 of 5 panelists indicated foam staying power.
D: 2 of 5 panelists indicated foam staying power.
<Rinsing Ease>
A: All 5 panelists indicated ease of rinsing.
B: 4 of 5 panelists indicated ease of rinsing.
C: 3 of 5 panelists indicated ease of rinsing.
D: 2 of 5 panelists indicated ease of rinsing.
<Residue after Rinsing>
A: All 5 panelists indicated absence of residue.
B: 4 of 5 panelists indicated absence of residue.
C: 3 of 5 panelists indicated absence of residue.
D: 2 of 5 panelists indicated absence of residue.
<Greasiness after Drying>
A: All 5 panelists indicated absence of greasiness.
B: 4 of 5 panelists indicated absence of greasiness.
C: 3 of 5 panelists indicated absence of greasiness.
D: 2 of 5 panelists indicated absence of greasiness.
<Moist Feeling after Drying>
A: All 5 panelists indicated presence of moist feeling.
B: 4 of 5 panelists indicated presence of moist feeling.
C: 3 of 5 panelists indicated presence of moist feeling.
D: 2 of 5 panelists indicated presence of moist feeling.
The evaluation results are shown in Tables 1 to 3.

TABLE 1

| Table | | | | | | | | (wt %) |
|---|---|---|---|---|---|---|---|---|
| | | | | Examples | | | | |
| 1 | Component | 1 | 2 | 3 | 4 | 5 | 6 |
| a | Stearic acid[*1] | 18 | 18 | 18 | 18 | 18 | 18 |
| | Lauric acid[*2] | 5 | 5 | 5 | 5 | 5 | 5 |
| | Myristic acid[*3] | 9 | 9 | 9 | 9 | 9 | 9 |
| | Cocamidopropyl betaine (30%)[*4] | 4 | 4 | 4 | 4 | 4 | 4 |
| | Na methyl cocoyl taurate (30%)[*5] | 2 | 2 | 2 | 2 | 2 | 2 |
| | Dipentaerythrityl tripolyhydroxystearate[*6] | 2 | — | — | — | — | — |
| | Polyhydroxystearic acid[*7] | — | 0.5 | 1 | 2 | 4 | 6 |
| b | Glycerin | 6 | 6 | 6 | 6 | 6 | 6 |
| | Dipropylene glycol | 5.5 | 5.5 | 5.5 | 5.5 | 5.5 | 5.5 |
| | Sorbitol (70% aq) | 2 | 2 | 2 | 2 | 2 | 2 |
| | PEG-400[*8] | 12.5 | 12.5 | 12.5 | 12.5 | 12.5 | 12.5 |
| | Self-emulsifying glyceryl monostearate[*9] | 1 | 1 | 1 | 1 | 1 | 1 |
| | EDTA-2Na | 0.05 | 0.05 | 0.05 | 0.05 | 0.05 | 0.05 |
| | KOH (50%) | 11.6 | 11.6 | 11.6 | 11.6 | 12.3 | 12.4 |
| | Water | 21.35 | 22.85 | 22.35 | 21.35 | 18.65 | 16.55 |
| Total | | 100 | 100 | 100 | 100 | 100 | 100 |
| Lathering ease | | A | B | B | A | A | A |
| Foam fineness | | A | B | A | A | A | A |
| Foam elasticity (viscosity) | | A | B | B | A | A | A |
| Foam staying power | | B | B | B | B | B | B |
| Rinsing ease | | A | B | B | A | A | A |
| Residue after rinsing | | B | B | A | A | A | A |
| Greasiness after drying | | B | B | B | B | B | B |
| Moist feeling after drying | | A | A | A | A | A | A |

[*1]NAA-180 (NOF CORPORATION)
[*2]LUNAC L-98 (Kao Chemicals)
[*3]NAA-142 (NOF CORPORATION)
[*4]Rebon 2000 (Sanyo Chemical Industries Ltd.)
[*5]Nikkol CMT-30 (Nikko Chemicals Co., Ltd.)
[*6]SALACOS WO-6 (Nisshin Oillio Group Ltd.)
[*7]SALACOS HS-6C (Nisshin Oillio Group Ltd.)
[*8]PEG-400 (Sanyo Chemical Industries Ltd.)
[*9]Emalex GMS-ASE (NIHON EMULSION Co., Ltd.)

TABLE 2

(wt %)

| Table 2 | Component | Comparative Examples |||||| 
|---|---|---|---|---|---|---|---|
| | | 1 | 2 | 3 | 4 | 5 | 6 |
| a | Stearic acid*1 | 18 | 18 | 18 | 18 | 18 | 18 |
| | Lauric acid*2 | 5 | 5 | 5 | 5 | 5 | 5 |
| | Myristic acid*3 | 9 | 9 | 9 | 9 | 9 | 9 |
| | Cocamidopropyl betaine (30%)*4 | 4 | 4 | 4 | 4 | 4 | 4 |
| | Na methyl cocoyl taurate (30%)*5 | 2 | 2 | 2 | 2 | 2 | 2 |
| | Triethylhexanoin*6 | — | 2 | — | — | — | — |
| | Polyglyceryl monoisostearate*7 | — | — | 2 | — | — | — |
| | Trehalose isostearate esters*8 | — | — | — | 2 | — | — |
| | Olive oil | — | — | — | — | 2 | — |
| | Vaseline*9 | — | — | — | — | — | 2 |
| b | Glycerin | 6 | 6 | 6 | 6 | 6 | 6 |
| | Dipropylene glycol | 5.5 | 5.5 | 5.5 | 5.5 | 5.5 | 5.5 |
| | Sorbitol (70% aq) | 2 | 2 | 2 | 2 | 2 | 2 |
| | PEG-400*10 | 12.5 | 12.5 | 12.5 | 12.5 | 12.5 | 12.5 |
| | Self-emulsifying glyceryl monostearate*11 | 1 | 1 | 1 | 1 | 1 | 1 |
| | EDTA-2Na | 0.05 | 0.05 | 0.05 | 0.05 | 0.05 | 0.05 |
| | KOH (50%) | 11.6 | 11.6 | 11.6 | 11.6 | 12.3 | 12.4 |
| | Water | 21.35 | 21.35 | 21.35 | 21.35 | 21.35 | 21.35 |
| | Total | 100 | 100 | 100 | 100 | 100 | 100 |
| | Lathering ease | B | C | D | D | D | D |
| | Foam fineness | C | C | C | C | B | C |
| | Foam elasticity (viscosity) | C | D | D | D | C | D |
| | Foam staying power | C | C | D | D | C | D |
| | Rinsing ease | B | C | C | C | C | C |
| | Residue after rinsing | B | D | D | C | D | C |
| | Greasiness after drying | B | C | C | C | C | C |
| | Moist feeling after drying | D | B | A | A | B | B |

*1 NAA-180 (NOF CORPORATION)
*2 LUNAC L-98 (Kao Chemicals)
*3 NAA-142 (NOF CORPORATION)
*4 Rebon 2000 (Sanyo Chemical Industries Ltd.)
*5 Nikkol CMT-30 (Nikko Chemicals Co., Ltd.)
*6 T.I.O (Nisshin Oillio Group Ltd.)
*7 SALACOS 41V (Nisshin Oillio Group Ltd.)
*8 NOMCORT TQ-5 (Nisshin Oillio Group Ltd.)
*9 NOMCORT W (Nisshin Oillio Group Ltd.)
*10 PEG-400 (Sanyo Chemical Industries Ltd.)
*11 Emalex GMS-ASE (NIHON EMULSION Co., Ltd.)

TABLE 3

(wt%)

| | Component | Comparative Examples ||
|---|---|---|---|
| | | 7 | 8 |
| a | Stearic acid*1 | 18 | 18 |
| | Lauric acid*2 | 5 | 5 |
| | Myristic acid*3 | 9 | 9 |
| | Cocamidopropyl betaine (30%)*4 | 4 | 4 |
| | Na methyl cocoyl taurate (30%)*5 | 2 | 2 |
| | 12-hydroxystearic acid | 2 | — |
| | Di(phytostearyl/octyldodecyl) lauroyl glutamate*6 | — | 2 |
| b | Glycerin | 6 | 6 |
| | Dipropylene glycol | 5.5 | 5.5 |
| | Sorbitol (70% aq) | 2 | 2 |
| | PEG-400*7 | 12.5 | 12.5 |
| | Self-emulsifying glyceryl monostearate*8 | 1 | 1 |
| | EDTA-2Na | 0.05 | 0.05 |
| | KOH (50%) | 11.6 | 11.6 |
| | Water | 21.35 | 21.35 |
| | Total | 100 | 100 |
| | Lathering ease | B | C |
| | Foam fineness | C | C |
| | Foam elasticity (viscosity) | B | B |
| | Foam staying power | D | C |
| | Rinsing ease | C | C |
| | Residue after rinsing | C | D |

TABLE 3-continued

| | | (wt%) |
|---|---|---|
| | Comparative Examples | |
| Component | 7 | 8 |
| Greasiness after drying | C | C |
| Moist feeling after drying | B | A |

*[1]NAA-180 (NOF CORPORATION)
*[2]LUNAC L-98 (Kao Chemicals)
*[3]NAA-142 (NOF CORPORATION)
*[4]Rebon 2000 (Sanyo Chemical Industries Ltd.)
*[5]Nikkol CMT-30 (Nikko Chemicals Co., Ltd.)
*[6]Eldew PS-203 (Ajinomoto Co., Inc.)
*[7]PEG-400 (Sanyo Chemical Industries Ltd.)
*[8]Emalex GMS-ASE (NIHON EMULSION Co., Ltd.)

As a result, the creamy cleansing foams of Examples 1 to 6 that contained dipentaerythrityl tripolyhydroxystearate or polyhydroxystearic acid all demonstrated favorable lathering ease, foam fineness, foam elasticity (viscosity), foam staying power, rinsing ease, residue after rinsing, greasiness after drying and moist feeling after drying.

In contrast, although the creamy cleansing foams of Comparative Examples 3 and 4 that contained polyglyceryl monoisostearate or trehalose isostearate esters demonstrated improved moist feeling after drying in comparison with the cream cleansing foam of Comparative Example 1 that did not contain these components, other evaluation parameters such as lathering ease were all poor.

In addition, although the creamy cleansing foams of Comparative Examples 2, 5, 6 and 7 that contained triethylhexanone, olive oil, vaseline or 12-hydroxystearic acid also demonstrated improved moist feeling after drying in comparison with the creamy cleansing foam of Comparative Example 1, many of the other evaluation parameters such as lathering ease were poor. In addition, although the creamy cleansing foam of Comparative Example 8 that contained di(phytostearyl/octyl decyl) lauroyl glutamate, which was indicated as an example of an oily agent having a hydration rate of 100% in Patent Document 3, demonstrated improved moist feeling after drying in comparison with the creamy cleansing foam of Comparative Example 1, lathering ease, rinsing ease, residue after rinsing and greasiness after drying were poor.

<Measurement of Hydration Rate>

Hydration rate was measured for trehalose isostearate esters, polyglyceryl monoisostearate, dipentaerythrityl tripolyhydroxystearate, polyhydroxystearic acid (12-hydroxystearic acid), triethylhexanoin, vaseline and olive oil.

(Measurement Method)

First, 5 g of the target sample were weighed out in a 300 mL stainless steel mug, and the weight of the aforementioned sample and propeller were recorded. Next, after heating the sample and purified water to 70° C., purified water was gradually added while stirring the sample with the propeller. Surplus water was removed by using for the endpoint the point at which purified water no longer entered, or in other words, the point at which water drained from the sample. Subsequently, the weight of the mug and propeller was again weighed, and hydration rate was calculated using the calculation formula indicated below.

Hydration rate (%)=([weight after measurement]−[weight before measurement]/[sample weight]×100

TABLE 4

| | Sample weight (g) | Weight before measurement (g) | Weight after measurement (g) | Hydration rate (%) |
|---|---|---|---|---|
| Trehalose isostearate esters*[1] | 5.05 | 446.92 | 470.17 | 460.40 |
| Polyglyceryl 2-isostearate*[2] | 5.13 | 451.61 | 460.52 | 173.68 |
| Dipentaerythrityl tripolyhydroxystearate*[3] | 5.02 | 444.97 | 453.30 | 165.94 |
| Polyhydroxystearic acid*[4] | 5.16 | 450.72 | 451.95 | 23.84 |
| Triethylhexanoin*[5] | 5.05 | 449.50 | 449.50 | 0.00 |
| Vaseline*[6] | 5.00 | 448.99 | 448.99 | 0.00 |
| Olive oil | 5.09 | 446.01 | 446.01 | 0.00 |

*[1]NOMCORT TQ-5 (Nisshin Oillio Group Ltd.)
*[2]SALACOS 41V (Nisshin Oillio Group Ltd.)
*[3]SALACOS WO-6 (Nisshin Oillio Group Ltd.)
*[4]SALACOS HS-6C (Nisshin Oillio Group Ltd.)
*[5]T.I.O (Nisshin Oillio Group Ltd.)
*[6]NOMCORT W (Nisshin Oillio Group Ltd.)

The measurement and calculation results are shown in Table 4. As a result, among the dipentaerythrityl tripolyhydroxystearate and polyhydroxystearic acid used in Examples 1 to 6, although the hydration rate of dipentaerythrityl tripolyhydroxystearate was equal to or greater than 100%, the hydration rate of polyhydroxystearic acid was only 23.84%. On the basis of these results, it was clearly determined that the effects of the cleansing agent of the present invention, namely effects such as moist feeling after drying, are not dependent on the hydration rate of the substance added to the cleansing agent.

Examples 7 to 9

(Production Method)

Cleansing foams were obtained according to the formulations shown in Table 5. More specifically, creamy cleansing foams were obtained using the same production method as Examples 1 to 3.

(Evaluation)

Each of the creamy cleansing foams was evaluated for lathering ease, foam fineness, foam elasticity (viscosity), foam staying power, rinsing ease, residue after rinsing, greasiness after drying and moist feeling after drying. The evaluation results are shown in Table 5.

TABLE 5

| | | | | (wt %) |
|---|---|---|---|---|
| | | | Examples | |
| | Component | 7 | 8 | 9 |
| a | Stearic acid*[1] | 18 | 18 | 18 |
| | Lauric acid*[2] | 5 | 5 | 5 |
| | Myristic acid*[3] | 9 | 9 | 9 |
| | Cocamidopropyl betaine(30%)*[4] | 4 | 4 | 4 |
| | Na methyl cocoyl taurate (30%)*[5] | 2 | 2 | 2 |
| | Polyhydroxystearic acid (dimer) | 2 | — | — |
| | Polyhydroxystearic acid (tetramer) | — | 2 | — |
| | Polyhydroxystearic acid (decamer) | — | — | 2 |
| b | Glycerin | 6 | 6 | 6 |
| | Dipropylene glycol | 5.5 | 5.5 | 5.5 |
| | Sorbitol (70% aq) | 2 | 2 | 2 |
| | PEG-400*[6] | 12.5 | 12.5 | 12.5 |
| | Self-emulsifying glyceryl monostearate*[7] | 1 | 1 | 1 |

TABLE 5-continued

| | | (wt %) | |
|---|---|---|---|
| | | Examples | |
| Component | 7 | 8 | 9 |
| EDTA-2Na | 0.05 | 0.05 | 0.05 |
| KOH (50%) | 11.6 | 11.6 | 11.6 |
| Water | 21.35 | 21.35 | 21.35 |
| Total | 100 | 100 | 100 |
| Lathering ease | B | A | A |
| Foam fineness | A | A | A |
| Foam elasticity (viscosity) | B | B | A |
| Foam staying power | B | B | B |
| Rinsing ease | B | A | A |
| Residue after rinsing | B | A | A |
| Greasiness after drying | B | B | B |
| Moist feeling after drying | B | B | A |

*[1]NAA-180 (NOF CORPORATION)
*[2]LUNAC L-98 (Kao Chemicals)
*[3]NAA-142 (NOF CORPORATION)
*[4]Rebon 2000 (Sanyo Chemical Industries Ltd.)
*[5]Nikkol CMT-30 (Nikko Chemicals Co., Ltd.)
*[6]PEG-400 (Sanyo Chemical Industries Ltd.)
*[7]Emalex GMS-ASE (NIHON EMULSION Co., Ltd.)

Example 10

Comparative Example 9

(Production Method)

Baby shampoos were obtained according to the formulations shown in Table 6. More specifically, all of the components shown in Table 6 were mixed and dissolved at 70° C. followed by cooling while stirring to obtain baby shampoos.

(Evaluation)

Each of the baby shampoos was evaluated for lathering ease, foam fineness, foam elasticity (viscosity), foam staying power, rinsing ease, residue after rinsing, greasiness after drying and moist feeling after drying. The evaluation results are shown in Table 6.

TABLE 6

| | | (wt%) |
|---|---|---|
| Component | Example 10 | Comparative Example 9 |
| Agar-xanthan gum mixture*[1] | 0.75 | 0.75 |
| Polyhydroxystearic acid (hexamer)*[2] | 2 | — |
| Cocamidopropyl betaine (30%)*[3] | 20 | 20 |
| Decyl glucoside (40%)*[4] | 5.6 | 5.6 |
| Hydroxyethyl urea (50%)*[5] | 5 | 5 |
| Glycerin | 5 | 5 |
| Pentylene glycol | 5 | 5 |
| Phenoxyethanol | 0.4 | 0.4 |
| EDTA-2Na | 0.01 | 0.01 |
| Water | 56.24 | 58.24 |
| Total | 100 | 100 |

TABLE 6-continued

| | | (wt%) |
|---|---|---|
| Component | Example 10 | Comparative Example 9 |
| Lathering ease | A | B |
| Foam fineness | A | C |
| Foam elasticity (viscosity) | B | C |
| Foam staying power | B | C |
| Rinsing ease | A | C |
| Residue after rinsing | A | C |
| Greasiness after drying | B | C |
| Moist feeling after drying | A | C |

*[1]NOMCORT AG (Nisshin Oillio Group Ltd.)
*[2]SALACOS HS-6C (Nisshin Oillio Group Ltd.)
*[3]Rebon 2000 (Sanyo Chemical Industries Ltd.)
*[4]Midol 10 (Kao Corporation)
*[5]Hydrovance (Akzonobel)

As a result, the baby shampoo of Example 10 that contained polyhydroxystearic acid (hexamer) demonstrated favorable lathering ease, foam fineness, foam elasticity (viscosity), foam staying power, rinsing ease, residue after rinsing, greasiness after drying and moist feeling after drying in comparison with the baby shampoo of Comparative Example 9 that did not contain polyhydroxystearic acid (hexamer).

INDUSTRIAL APPLICABILITY

The composition for a cleansing agent of the present invention can be preferably used in the production fields of various cleansing agents.

The invention claimed is:

1. A cleansing agent, comprising:
a component (A) in the form of one or more types of surfactants selected from the group consisting of an anionic surfactant and an amphoteric surfactant, a component (B) in the form of a hydroxystearic acid polymer, a component (C) in the form of a dispersion medium, and water, wherein an average number of monomers of the hydroxystearic acid polymer is 4 to 12.

2. The cleansing agent according to claim 1, wherein an amount of the component (A) is 5 to 60% by weight, relative to a total amount of the cleansing agent.

3. The cleansing agent according to claim 1, wherein an amount of the component (B) is 0.1 to 15% by weight, relative to the total amount of the cleansing agent.

4. The cleansing agent according to claim 1, wherein the component (B) comprises polymers of 12-hydroxystearic acid.

5. The cleansing agent according to claim 1, wherein the component (C) is a polyvalent alcohol.

6. The cleansing agent according to claim 5, wherein the polyvalent alcohol is one or more polyvalent alcohols selected from the group consisting of propylene glycol, glycerin, diglycerin, 1,3-butylene glycol, isoprene glycol, dipropylene glycol, polyethylene glycol, pentaerythritol, dipentaerythritol, neopentyl glycol, sorbitol, and sorbitan.

* * * * *